United States Patent
Witthaus et al.

(10) Patent No.: US 6,832,981 B2
(45) Date of Patent: Dec. 21, 2004

(54) TUBE ARRANGEMENT AND A METHOD FOR ITS MANUFACTURE

(75) Inventors: Friedrich Witthaus, Namborn (DE); Wolfram Weber, Spiesen-Elversberg (DE)

(73) Assignee: Fresenius HemoCare GmbH, Bad Homburg (DE)

( * ) Notice: Subject to any disclaimer, the term of this patent is extended or adjusted under 35 U.S.C. 154(b) by 44 days.

(21) Appl. No.: 10/152,674

(22) Filed: May 23, 2002

(65) Prior Publication Data

US 2002/0195154 A1 Dec. 26, 2002

(30) Foreign Application Priority Data

Jun. 20, 2001 (DE) .......................... 101 29 769

(51) Int. Cl.[7] .............................................. B04B 11/00
(52) U.S. Cl. ........................... 494/18; 494/83; 138/111
(58) Field of Search ........................ 138/111, 119, 138/177, 109; 494/18, 83

(56) References Cited

U.S. PATENT DOCUMENTS

| | | | | | |
|---|---|---|---|---|---|
| 2,832,374 | A | * | 4/1958 | November .............. 285/123.1 |
| 2,936,791 | A | * | 5/1960 | Farrar ...................... 285/114 |
| 3,526,086 | A | * | 9/1970 | Morgan .................... 138/111 |
| 3,646,972 | A | * | 3/1972 | Kuypers .................... 138/111 |
| 4,230,263 | A | * | 10/1980 | Westberg ................... 494/45 |
| 4,372,484 | A | * | 2/1983 | Larsson et al. ............ 494/14 |
| 4,389,207 | A | * | 6/1983 | Bacehowski et al. ....... 494/42 |
| 4,439,178 | A | * | 3/1984 | Mulzet ....................... 494/85 |
| 4,459,169 | A | * | 7/1984 | Bacehowski et al. ....... 156/221 |
| 4,865,081 | A | * | 9/1989 | Neumann et al. .......... 138/111 |
| 4,963,420 | A | * | 10/1990 | Jarrin et al. ............... 428/36.9 |
| 5,362,291 | A | * | 11/1994 | Williamson, IV ........... 494/18 |
| 5,514,069 | A | * | 5/1996 | Brown et al. ............... 494/18 |
| 5,989,177 | A | * | 11/1999 | West et al. ................. 494/46 |
| 6,273,849 | B1 | * | 8/2001 | Scherer ..................... 494/37 |
| 6,344,020 | B1 | * | 2/2002 | Reitz et al. ................ 494/46 |
| 6,716,154 | B2 | * | 4/2004 | Witthaus et al. ........... 494/83 |

FOREIGN PATENT DOCUMENTS

| | | |
|---|---|---|
| DE | 26 12 988 | 10/1976 |
| DE | 32 42 541 | 5/1984 |
| DE | 36 32 241 | 6/1988 |
| DE | 42 20 232 | 12/1993 |
| DE | 198 03 534 | 8/1999 |
| DE | 19803535 | 8/1999 |
| EP | 0 112 990 | 7/1984 |
| WO | 95/17261 | 6/1995 |
| WO | 01/30505 | 5/2001 |

* cited by examiner

Primary Examiner—James Hook
(74) Attorney, Agent, or Firm—Jacobson Holman PLLC

(57) ABSTRACT

A multi-lumen tube arrangement for use in a centrifuge free of a sliding seal, the tube arrangement having at least two individual tubes which are rotated around one another around their longitudinal and/or their parallel axes. The rotation of the tubes takes place in this connection in opposite directions starting from a support position disposed approximately centrally in order to compensate the torques applied to the tube arrangement. A method for manufacturing such a tube arrangement is also decribed.

17 Claims, 2 Drawing Sheets

TUBE ARRANGEMENT AND A METHOD FOR ITS MANUFACTURE

BACKGROUND OF THE INVENTION

1. Field of the Invention

The invention relates to a multi-lumen tube arrangement for use in a centrifuge free of a sliding seal and to a method for its manufacture, with the tube arrangement being rotated in the opposite direction towards its ends starting from a support position.

2. Description of the Related Art

Centrifuges free of sliding seals are known from the prior art, for example from DE 32 42 541 or DE 42 20 232. In this connection, a substance is broken down into its component parts and transported into separate containers via tubes. Since the containers are stationary, while the separation unit rotates, different solutions are known as to how the tube connection between the two should be guided. If one would like to dispense with a sliding seal in order to avoid contamination, the use of the above-mentioned centrifuges presents itself.

As represented in DE 26 12 988, the multi-lumen tube can consist of a single tube with a plurality of liquid channels, whereas DE 36 32 241 shows a tube arrangement of a plurality of individual tubes. In a centrifuge free of a sliding seal, the tubes or the multi-lumen tube arrangement are guided from a stationary connection point in a loop around the separation unit to the opposite side of the separation unit.

During operation of the centrifuge free of a sliding seal, the tube arrangement is connected to a drive unit which rotates at half the angular velocity or speed of the separation unit; furthermore, the tube arrangement rotates around itself. As a consequence of the different speeds between the drive unit and the separation unit, the tube arrangement untwines.

In this connection, the tube side lying radially further outside comes onto the inside and vice versa so that the whole tube arrangement is fulled. The outwardly disposed tube side is stretched while the inwardly disposed side is compressed, since the paths from the stationary connection up to the separation unit have a different length. For this reason, it is proposed in DE 36 32 241, to which reference is expressly made here, to wind individual tubes or tube lumens n+½ times around the longitudinal axis of the tube or its parallel axes to make the path distances equal on average.

Furthermore, the tube arrangement is subject to high mechanical strain due to the centrifugal forces and this strain grows as the speed increases. The line forms an outwardly overhanging loop which is exposed to high flexural forces and/or abrasion forces at its ends. For this reason, the tubes are frequently supported in centrifuges free of sliding seals such as described in DE 198 03 534. These bearings can be roller bearings as in WO 95/17261 or plain bearings as in EP 0 112 990.

In a tube arrangement of a centrifuge free of sliding seals, a torque arises at the support position due to the bearing friction which has to be transmitted to the support position from both hose ends. This torque produces an additional strain on the tube in that it counters the torsion resistance of the tube and thus the service life.

SUMMARY OF THE INVENTION

It is the object of the present invention to further develop a tube arrangement of the kind first mentioned such that service life is further clearly increased while still allowing a cost-favourable manufacture. This object is solved by a multi-lumen tube arrangement for use in a centrifuge free of a sliding seal having at least two tubes of of aporoximately equal length, the individual tubes being rotated free of tension around their longitudinal axes and/or their parallel axes and being fixed at their ends. The tube arrangement has a support position and the individual tubes are wound around one another in opposite directions from the support position, with the tubes being fixed at their ends and to the support position. A method of manufacturing such a tube arrangement is also shown.

The tube arrangement in accordance with the invention consists of at least two individual tubes, which are rotated about one another about their longitudinal axes or their parallel axes and are fixed at their ends, and which has a support position from where the tubes are rotated around one another in the opposite direction up to their ends.

As a result of the desired untwining of the tube arrangement, the torque transmitted from the separation unit to the bearing is counter to that from the stationary position to the bearing. It has been found that the stability or service life of the tube arrangement suffers when the transmitted torque acts in the opposite direction to the tube rotation. Trials were therefore carried out which measure the service life of the tube arrangement in dependence on the rotational direction of the two tube ends starting from the bearing. The trials document a substantially increased stability when the torque acting on the tube arrangement extends in the same direction as the rotation of the individual hoses around one another, in each case starting from the support position to their two fixed ends. Since, as described above, the torques act opposite to one another, the rotation of the tubes around their longitudinal axes and/or around their parallel axes, continuing from the support position, is likewise in the opposite direction in accordance with the invention.

The tube arrangement can, as described in the prior art, consist of one tube with a plurality of lumens, which are then likewise wound around their longitudinal axes, or of a plurality of individual tubes. For reasons of simplicity, a multi-lumen tube arrangement having at least two individual tubes is spoken of here, where, however, a multi-lumen tube having more than two lumen is to be subsumed, with the individual lumen then extending in accordance with the invention in an opposite spiral shape starting from the support position.

The tubes used in accordance with the invention consist of a polymer material of one or more layers such as polyamide, polyurethane or PVC as well as in particular polyolefins such as polyethylenes or polypropylenes and their blends, with different materials being able to be used in different layers.

If the tubes are used in the medical sector, bio-compatible materials are naturally more suitable. Whereas, in the past, PVC tubes were common, polyolefin tubes have come into use in the meantime, preferably multi-layer polyolefin tubes whose hardness in each layer can be set by blends, also with ethylene styrenes.

The tube arrangement in accordance with the invention has a high strength with respect to elongation, kinking or turning by a suitable choice of the polymer materials and of the layers used—whether in the form of extruded tubes or of laminated tubes. The inner diameter can also be kept constant substantially over the overall length so that there is no risk of clogging.

Such a tube arrangement usually consists of two to five lumens or single tubes, preferably four. The individual tubes are turned around the longitudinal axis of the tube arrangement or around a parallel axis hereto at least in partial regions so that a bundle twisted into itself is created. In this connection the twisting takes place according to conventional methods of stranding or braiding.

In this connection, the tube arrangement is fixed to the support position by clamping or bonding, for example, whereas the ends are disposed at holding pieces whose receiving bores still allow the movement of the individual tubes, that is are a little larger than the tube diameter so that an untwisting can take place. The individual tubes are thereby not under additional tension, which likewise reduces the service life of the tubes. In this connection, the turning preferably takes place n+½ times, with n being zero or an integer. The individual tubes are particularly preferably turned 1.5 times.

In this connection, the individual tubes are fixed at the support position and the holding pieces, in which the individual tubes are first loosely held, are displaced towards the support position, rotated and pushed back into their starting position. The ends are then fixed in place, either by clamping into the holding piece or bonding in the holding piece or bonding the individual tubes.

In this connection, the manufacturing method is not limited to the procedure described above, but can naturally also take place in that the ends are already fixed in place, while the support position is pressed toward the holding piece, is turned and displaced back into its starting position again. In this connection, the bearing must have bores which are so large that they allow a separate movement of the tubes and avoid the twisting of the individual tubes around one another. Since, due to the turning of the support position, only one movement has to take place, with which simultaneously both tube parts are rotated in opposite directions, this simpler manufacturing method is preferred.

BRIEF DESCRIPTION OF THE DRAWINGS

Further details and advantages of the invention result from an embodiment shown in the drawing.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
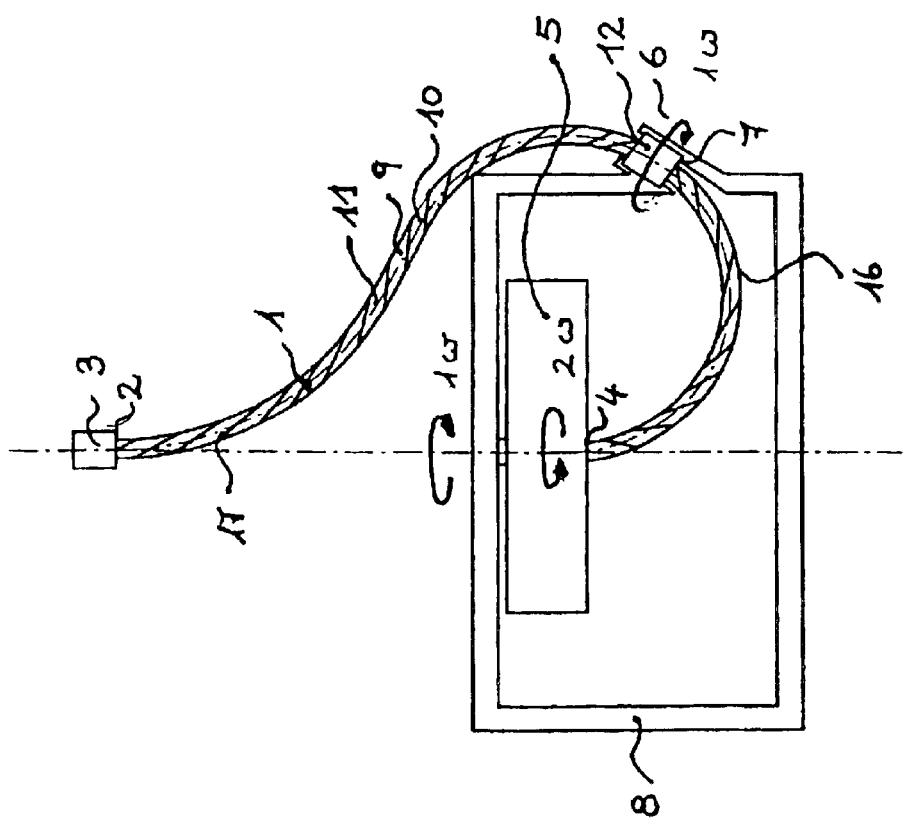
FIG. 1 shows a tube arrangement in a centrifuge free of a sliding seal.

The tube guidance in a centrifuge free of a sliding seal is shown schematically in FIG. 1. In this connection, the tube arrangement 1 is fixed at its first end 2 to a stationary position 3 and secured at its second end 4 to a separation unit 5. The tube arrangement is held at a support position 6 by means of a bearing holder 12 of a plain bearing 7 which is in turn supported in a rotation frame 8. When the separation unit 5 rotates at an angular velocity of 2ω, the tube arrangement secured to this separation unit at the position 4 is turned along. At the same time, the rotation frame 8 guides the tube arrangement 1 around the separation unit 5 in that the whole rotation frame 8 rotates at an angular velocity of 1ω in the opposite direction to the separation unit 5. The tube arrangement 1 turns around itself also at 1ω so that the sum of the angular velocities of the tube guidance to that of the separation unit cancel out and therefore no twisting and/or no shearing off takes place, for example at the stationary fixing 2.

A torque is transmitted to the tube arrangement 1 by the rotation of the separation unit 5 and said torque acts oppositely to the torque which is transmitted from the stationary fixing 2 onto the tube arrangement since the tube arrangement extends more or less in a U-shaped manner. So that the rotation of the individual tubes 9 and 10 is not allowed to act counter to the torque, the individual tubes 9, 10 are wound, braided or turned in the same direction around their longitudinal axes 11 and/or their parallel axes as the action of the torque in the partial sections 16, 17 of the tube arrangement, in each case seen starting from the support position 6 to their ends 2 and 4.

Figure 2:
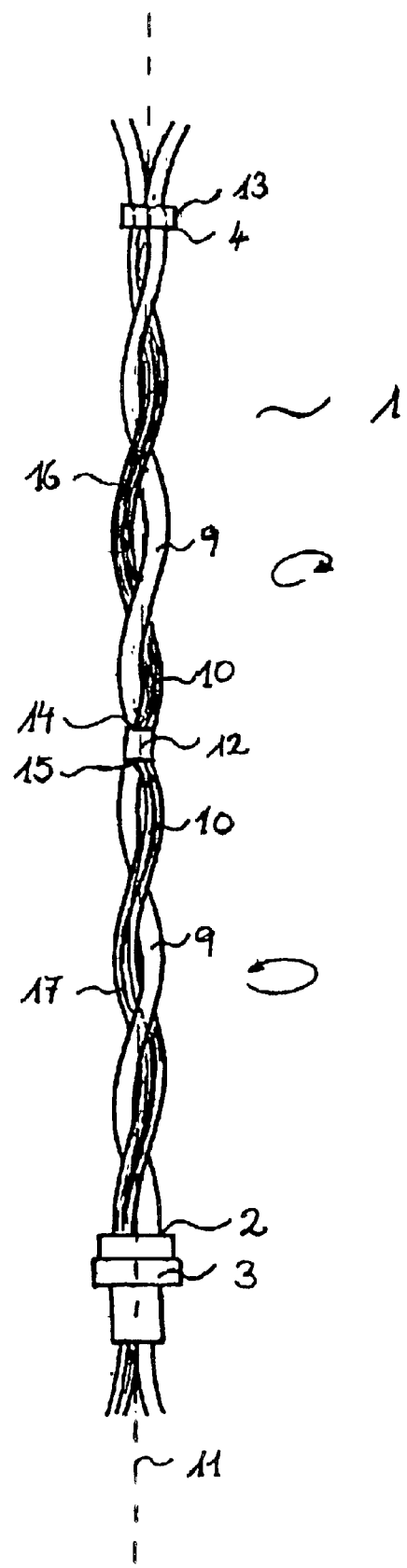
FIG. 2 shows the elongated tube arrangement with individual tubes rotated in the opposite direction starting from the support position.

FIG. 2 shows the tube arrangement 1 in the elongate state. The individual tubes 9 and 10 are rotated about their longitudinal axes 11 in the counter-rotation direction to their ends 2 and 4 starting from the support position 12. In this connection, the ends are fixed in a holder 3 or 13 and in its bearing holder 12 so that no unturning can take place. In this connection, the individual tubes are preferably wound around one another in n+½ turns, with n being 0 or an integer so that the ends of the individual tubes 4, 2 each come to rest at the side offset by 180° to their ends 14 and 15 secured to the bearing holder 12. In this way, each individual hose or each lumen has approximately the same length. Each partial piece 16, 17 of the tube arrangement 1 preferably has a one and a half times turn.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. In combination, a centrifuge free of a sliding seal, a multi-lumen tube having a plurality of individual tubes of approximately equal length that are rotated free of tension around longitudinal axes thereof, and a holding element fixing said individual tubes of said multi-lumen tube at a support position along said tube length between ends thereof, said holding element being supported in a rotation frame of said centrifuge at said support position such that two partial sections of said tube length on either side of said support position are inside and outside of said rotation frame, respectively, said rotation frame guiding said multi-lumen tube around a separation unit which rotates in a direction opposite to rotation of said rotation frame, said individual tubes being wound around one another in opposite directions beginning from the support position and being fixed at said ends so that opposing torque action imposed on the two partial sections corresponds with the respective winding directions of said partial sections.

2. The combination as set forth in claim 1, wherein the ends of the tubes are rotated through n½ turns with respect to said support position, where n is 0 or an integer.

3. The combination as set forth in claim 2, wherein the tube rotation is approximately 1.5 turns.

4. The combination as set forth in claim 2, wherein the holding element is a bearing holder having a plain bearing.

5. The combination as set forth in claim 2, wherein the holding element is a bearing holder having a roller bearing.

6. The combination as set forth in claim 2, wherein the ends are fixed by holding pieces, and said holding pieces and said holding element each have a plurality of bores to receive the individual tubes.

7. The combination as set forth in claim 1, wherein said plurality of tubes is composed of four individual tubes.

8. A method for manufacturing a multi-lumen tube having a plurality of tubes and for incorporating said multi-lumen tube within a centrifuge free of a sliding seal, comprising the steps of:

clamping at least two individual tubes of approximately equal length at a support position located between ends of said tubes to divide the tube length into first and second partial sections;

rotating without tension said individual tubes of the first partial section around a longitudinal axis thereof in a first direction beginning from said support position, said first partial section being rotated through approximately n½ turns with respect to said support position;

rotating without tension said individual tubes of the second partial section around a longitudinal axis thereof in a second direction opposite said first direction beginning from said support position, said second partial section being rotated through approximately n½ turns with respect to said support position;

fixing the ends of the tubes with holding pieces;

securing one end of the tubes to a stationary fixing outside the centrifuge and the other end of the tubes to a separation unit within a rotation frame of said centrifuge, said separation unit and said rotation frame rotating in opposite directions; and supporting the tubes in said rotation frame at said support position so that said first and second partial sections are inside and outside of said rotation frame, respectively, the opposite rotation directions of said first and second partial sections corresponding to respective opposing torque actions imposed by said stationary fixing and said separation unit.

9. The method as set forth in claim 8, wherein the steps of rotating include holding the individual tubes loosely in a starting position, pushing the tubes toward the support position, twisting the tubes, and pushing the tubes back to the starting position.

10. The method as set forth in claim 8, wherein the steps of rotating include holding the individual tubes loosely in a starting position, pushing the tubes toward the holding pieces, twisting the tubes, and pushing the tubes back to the starting position.

11. In combination, a centrifuge free of a sliding seal, a multi-lumen tube having a plurality of individual tubes of approximately equal length that are rotated free of tension around longitudinal axes thereof, and a holding element fixing said individual tubes of said multi-lumen tube at a support position located approximately midway along said tube length between first and second ends thereof, said holding element dividing the tube length into two partial sections and being supported in a rotation frame of said centrifuge, the individual tubes of the first partial section being wound around one another from the support position to said first ends in a direction opposite to a winding of the tubes of the second partial section around one another from the support position to said second ends to compensate for opposing torque applied to said multi-lumen tube by a separation unit within said rotation frame to which said first ends are secured and a stationary fixing of said second ends outside said centrifuge, said tubes being fixed at said first and second ends by holding pieces.

12. The combination as set forth in claim 11, wherein said holding pieces and said holding element each have a plurality of bores to receive the individual tubes.

13. The combination as set forth in claim 11, wherein the ends of the tubes are rotated through n½ turns with respect to said support position, where n is 0 or an integer.

14. The combination as set forth in claim 11, wherein the tube rotation is approximately 1.5 turns.

15. The combination as set forth in claim 11, wherein the holding element is a bearing holder having a plain bearing.

16. The combination as set forth in claim 14, wherein the holding element is a bearing holder having a roller bearing.

17. The combination as set forth in claim 11, wherein said plurality of tubes is composed of four individual tubes.

* * * * *